(12) United States Patent
Petit (10) Patent No.: US 9,572,604 B2
(45) Date of Patent: Feb. 21, 2017

(54) INSTRUMENT KIT FOR SPINAL OSTEOSYNTHESIS

(71) Applicant: SAFE ORTHOPAEDICS, Eragny sur Oise (FR)

(72) Inventor: Dominique Petit, Verton (FR)

(73) Assignee: Safe Orthopaedics, Eragny sur Oise (FR)

( * ) Notice: Subject to any disclaimer, the term of this patent is extended or adjusted under 35 U.S.C. 154(b) by 0 days.

(21) Appl. No.: 14/389,828

(22) PCT Filed: Apr. 2, 2013

(86) PCT No.: PCT/FR2013/050718
§ 371 (c)(1),
(2) Date: Oct. 1, 2014

(87) PCT Pub. No.: WO2013/150232
PCT Pub. Date: Oct. 10, 2013

(65) Prior Publication Data
US 2015/0066084 A1    Mar. 5, 2015

(30) Foreign Application Priority Data

Apr. 2, 2012    (FR) ...................... 12 52994

(51) Int. Cl.
*A61B 17/70*    (2006.01)
*A61B 17/86*    (2006.01)

(52) U.S. Cl.
CPC ......... *A61B 17/7076* (2013.01); *A61B 17/708* (2013.01); *A61B 17/7032* (2013.01); *A61B 17/8605* (2013.01); *A61B 2090/037* (2016.02)

(58) Field of Classification Search
CPC .................. A61B 17/708; A61B 17/7086
(Continued)

(56) References Cited

U.S. PATENT DOCUMENTS 8,439,924 B1 *    5/2013    McBride .............. A61B 17/708
606/104
2004/0138662 A1    7/2004    Landry et al.
(Continued)

FOREIGN PATENT DOCUMENTS

| WO | 2007092870 A2 | 8/2007 |
| WO | 2009132110 A1 | 10/2009 |
| WO | 2011080426 A2 | 7/2011 |

*Primary Examiner* — Ellen C Hammond
*Assistant Examiner* — Stuart S Bray
(74) *Attorney, Agent, or Firm* — Bachman & LaPointe, P.C (57) ABSTRACT

A surgical kit for fastening vertebrae via the posterior approach or via the posterolateral approach, comprising: at least one vertebral or pedicle screw, and a fitting tube co-operating with the screw; the fitting tube having two rigid branches, each of the two branches having, on the inside face of its proximal end, at least one shoulder; the kit further comprising a retractable securing insert for securing together the branches; wherein the screw head has at least two longitudinal extensions, extending in the distal direction, each of said extensions being configured to enable said screw head to be inserted into a space of complementary shape formed between the inside surface of the proximal end of one of the rigid branches and the outside surface of the proximal end of said retractable insert, when the retractable insert is fully engaged in the fitting tube.

8 Claims, 7 Drawing Sheets (58) Field of Classification Search
USPC .................................................. 606/86 A
See application file for complete search history.

(56) References Cited

U.S. PATENT DOCUMENTS

| | | | |
|---|---|---|---|
| 2005/0131408 A1* | 6/2005 | Sicvol | A61B 17/7091 606/86 A |
| 2005/0192570 A1 | 9/2005 | Jackson | |
| 2006/0074418 A1 | 4/2006 | Jackson | |
| 2008/0077139 A1 | 3/2008 | Landry et al. | |
| 2008/0091213 A1* | 4/2008 | Jackson | A61B 17/7008 606/99 |
| 2008/0119849 A1* | 5/2008 | Beardsley | A61B 17/7032 606/306 |
| 2008/0125817 A1* | 5/2008 | Arnett | A61B 17/7002 606/319 |
| 2008/0191213 A1 | 8/2008 | Bae et al. | |
| 2009/0149892 A1* | 6/2009 | Stad | A61B 17/7077 606/86 A |
| 2010/0114179 A1* | 5/2010 | Moore | A61B 17/7032 606/308 |
| 2010/0249856 A1* | 9/2010 | Iott | A61B 17/7085 606/86 A |
| 2011/0087293 A1* | 4/2011 | Ferreira | A61B 17/708 606/265 |
| 2011/0196426 A1* | 8/2011 | Peukert | A61B 17/7083 606/279 |
| 2012/0016424 A1* | 1/2012 | Kave | A61B 17/7037 606/305 |
| 2012/0031792 A1* | 2/2012 | Petit | A61B 17/708 206/438 |
| 2012/0303055 A1* | 11/2012 | Marik | A61B 17/708 606/205 |
| 2013/0012999 A1* | 1/2013 | Petit | A61B 17/7076 606/279 |
| 2013/0053896 A1* | 2/2013 | Voyadzis | A61B 17/708 606/279 |
| 2013/0103094 A1* | 4/2013 | Beale | A61B 17/7076 606/279 |
| 2013/0245633 A1* | 9/2013 | Dauster | A61B 17/7076 606/104 |
| 2013/0245692 A1* | 9/2013 | Hayes | A61B 17/025 606/279 |
| 2013/0245705 A1* | 9/2013 | McBride | A61B 17/7032 606/86 R |
| 2014/0052187 A1* | 2/2014 | McBride | A61B 17/7085 606/264 |
| 2014/0277198 A1* | 9/2014 | Stad | A61B 17/7074 606/86 A |
| 2014/0277206 A1* | 9/2014 | Reitblat | A61B 17/7091 606/86 A |
| 2014/0379030 A1* | 12/2014 | Jackson | A61B 17/861 606/265 |
| 2015/0051648 A1* | 2/2015 | May | A61B 17/7086 606/264 |
| 2015/0051653 A1* | 2/2015 | Cryder | A61B 17/7004 606/86 A |
| 2015/0066042 A1* | 3/2015 | Cummins | A61B 17/7037 606/104 |
| 2015/0088210 A1* | 3/2015 | Reitblat | A61B 17/7082 606/86 A |
| 2015/0164495 A1* | 6/2015 | Petit | A61B 17/708 600/210 |
| 2015/0182265 A1* | 7/2015 | Biedermann | A61B 17/7085 606/265 |
| 2015/0190183 A1* | 7/2015 | Petit | A61B 17/7086 606/86 A |

\* cited by examiner

INSTRUMENT KIT FOR SPINAL OSTEOSYNTHESIS

BACKGROUND

The invention relates to an instrument kit making it possible to achieve spinal stabilization by means of a bone anchor element of the screw type via the posterior approach or via the posterolateral approach.

The instrument kit of the invention is designed particularly, but not exclusively, for lumbar, thoracic, or indeed posterior cervical spinal osteosynthesis surgery via minimally invasive surgery or open surgery.

When anatomical dysfunctions occur in the vertebral column, bone anchors of the vertebral or pedicle screw type are put in place in the vertebrae and are connected together by link elements of the rod or plate type.

In a particular application, the invention relates to the field of single-use instrument sets, packaged in sterile manner, and comprising all of the tools necessary for performing a surgical operation of fitting pedicle screws without using additional instruments.

In the prior art, a spinal device is described in US Patent Application US2004/138662, that device being constituted by a split tube having, at its distal end, means for fastening to a screw. The distal end is hinged via a hinge making it possible to move the proximal ends of the two branches apart so as to release the head of the screw and so as to enable the tube to be removed after the screw has been implanted.

In the meaning of the present invention, the term "proximal" is used to designate the end closer to the spinal operation zone and thus the end that is further away from the operator, and the term "distal" is used to designate the end that is opposite from the spinal zone, and thus that is accessible for the operator. The screw is fastened to the "proximal" end.

International Patent Application WO2007/092870 describes another solution for a spinal device, formed by a tube having a grabber-type clamp at its proximal end.

US Patent Application US2005/0192570 proposes another embodiment of a spinal device constituted by a tube having a longitudinal slot and a split proximal end making it possible to fasten a screw to it and to release the screw by moving the proximal end apart.

Such prior art solutions that propose to release the screw by moving the proximal ends of the screw-carrier tube apart are unsatisfactory because they require sufficient space, in the zone around the screw, for enabling it to be detached. Unfortunately, in that zone, the presence of the bone portion often limits the available space, and can give rise to difficulties for releasing the tube relative to the head of the screw.

In addition, the forces that need to be transmitted for radially disengaging the proximal end of the tube relative to the head of the screw are high and transmitting them involves manipulation that is not ergonomic and that needs to be performed remotely. Releasing the screw involves actions that can also mask the intervention zone during this difficult phase of the operation.

Finally, the Applicant's international patent application WO2011/080426 describes a surgical kit for fastening vertebrae via the posterior approach or via the posterolateral approach, that kit comprising at least one vertebral or pedicle screw, and a fitting tube co-operating with said screw, that kit being characterized in that:
said fitting tube is made up of two rigid independent tubes;
on the inside face of its proximal end, each of the tubes has a shoulder of shape complementary to the shape of an indentation provided on either side of the screw head, in order to allow said screw to be taken hold of, or to be released by moving the distal ends of said tubes apart;
the kit further comprising a retractable securing insert for securing together said tubes; and
said retractable securing insert having longitudinal fastening means arranged to be dovetail shaped so as to come into engagement with complementary slideways provided in said rigid tubes.

The various solutions proposed in the prior art suffer from a major drawback: when the surgeon exerts large forces on the tubes in order to correct the positions of the vertebrae into which the screws are engaged, the proximal ends of the tube can become detached from the screw, or, when the tube is made of a plastic material, for single-use applications, can break.

SUMMARY

An object of the invention is to propose a kit making it possible to improve the operation technique.

Such a kit is used as follows: the surgeon inserts the tube carrying the screw through an incision made in the dorsal zone. Once the screw is positioned in the pedicle of the vertebra, the surgeon anchors the screw by means of a screwdriver shank passing through the tube. The head of the screw remains secured to the proximal end of the tube. The surgeon can then act on the end of the tube used as a lever, so as to correct the relative angular positioning of the vertebrae. The forces to be applied are high, particularly when vertebrae have been injured due to major traumas. Such forces should be transmitted without causing the head of the screw to become disengaged, or causing the proximal ends of the tubes to break.

The prior art solutions do not make it possible to solve this problem.

In order to mitigate that drawback, the invention, in its most general embodiment, provides a surgical kit for fastening vertebrae via the posterior approach or via the posterolateral approach, said surgical kit comprising:
at least one vertebral or pedicle screw, and a fitting tube co-operating with said screw;
said fitting tube having two rigid branches, each of said two branches having, on the inside face of its proximal end, at least one shoulder of shape complementary to the shape of an indentation provided on either side of the screw head, for allowing said screw to be taken hold of, or to be released by moving the ends of said rigid branches apart;
the kit further comprising a retractable securing insert for securing together said branches;
said surgical kit being characterized in that said screw head has at least two longitudinal extensions, extending in the distal direction, each of said extensions being configured to enable it to be received in a space of complementary shape formed between the inside surface of the proximal end of one of the rigid branches and the outside surface of the proximal end of said retractable insert, when said retractable insert is fully engaged in said fitting tube.

Preferably, the head of the screw is provided with two break zones below said extensions.

Advantageously, said retractable securing insert has longitudinal fastening means arranged to be dovetail shaped so as to come into engagement with complementary slideways provided in said rigid branches.

In a variant, each of the distal ends of the branches is also provided with at least one tenon that comes to be received in a complementary cavity provided in the other branch.

In another variant, said screw head is provided with fork-shaped longitudinal extensions, and the branches are provided with spaces of shape complementary to the shape of said extensions.

In a particular embodiment, said screw head is provided with extensions made of polymer, each of which forms two prongs coming to be engaged in cavities defined firstly by respective ones of the branches, and secondly by the insert.

According to another particular embodiment, the head of the screw is further provided with a radial groove suitable for co-operating with lips formed on the inside surfaces of the proximal ends of the branches.

Preferably, said branches and said insert are made of a molded polymer material and are for single use.

The invention also provides a surgical screw for fastening vertebrae via the posterior approach or via the posterolateral approach, said screw being designed to be implanted using a tubular instrument formed of two branches, said surgical screw being characterized in that it has a head provided with at least two longitudinal extensions, extending in the distal direction, each of said extensions being configured to be suitable for being received in a space of complementary shape formed between the inside surface of the proximal end of one of the rigid branches and the outside surface of the proximal end of said retractable insert, when said insert is fully engaged in said fitting tube.

Preferably, the screw of the invention has a head that is provided with two break zones below said extensions.

BRIEF DESCRIPTION OF THE DRAWINGS

Other objects and advantages of the invention appear from the following description of a non-limiting embodiment of a kit of the invention, given with reference to the accompanying drawings, in which.

DETAILED DESCRIPTION

Figure 1:
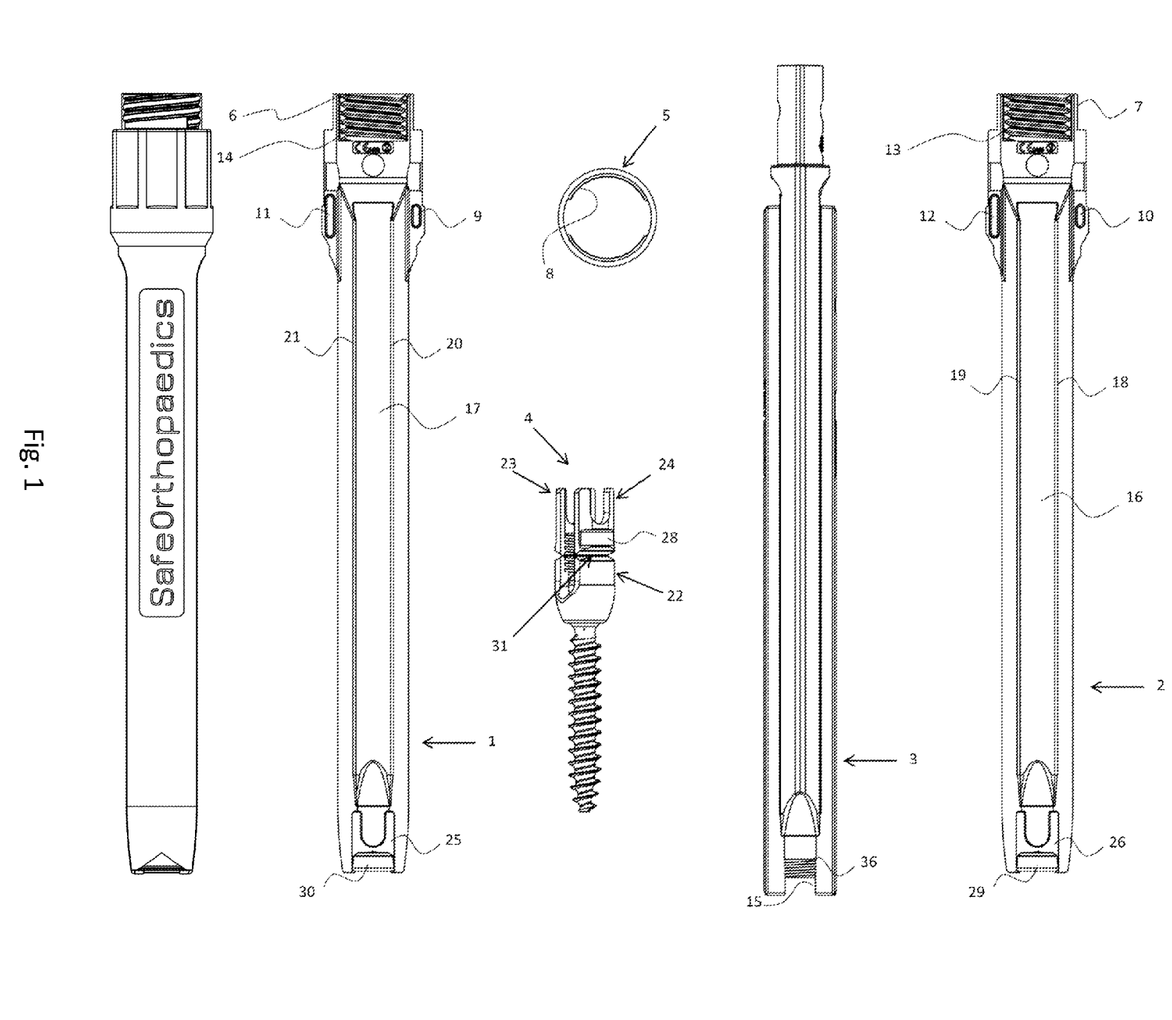
FIG. 1 is a view of the main components of an embodiment of an instrument kit of the invention.

FIG. 1 is a general view of the main components of a kit of the invention. The kit of the invention is constituted by two branch-shaped parts (1, 2), by a retractable securing insert or simply insert (3), by a screw (4), and by a ring (5). The kit further comprises a handle and a screwdriver shank that are not shown in FIG. 1.

In the example described, the two branches (1, 2) are constituted by molded semi-tubular parts that are made of polyarilamide reinforced with glass fibers. The distal end is provided with an outside thread (6, 7) designed to co-operate with inside tapping (8) of the ring (5). Each of the distal ends of the branches (1, 2) is also provided with at least one tenon (9, 10) that comes to be received in a complementary cavity (11, 12) provided in the other branch. When the two branches (1, 2) are assembled together, these tenons (9, 10) and the cavities (11, 12) guarantee that the threads of the two branches are positioned correctly to form a continuous thread enabling the ring (5) to be engaged and screwed thereon.

The branches (1, 2) that form the fitting tube (50) are also provided with tapping (13, 14) designed to receive a push handle (104) enabling the surgeon to exert, via the retractable securing insert (3), a longitudinal force on the intervertebral link rod (35) during the operation.

The retractable securing insert (3) is of quadrilobal cross-section, the shape of its cross-section being complementary to the inside cross-section of the fitting tube (50) formed when the two branches (1, 2) are assembled together. In the example described, it is also made by molding a polyarilamide that is, for example, reinforced with glass fibers.

The insert is engaged in an insertion canal formed by two longitudinal recesses (16, 17) in the branches (1, 2). These longitudinal recesses (16, 17) are defined on either side by slideways (18 to 21) co-operating with the insert by coupling of the "dovetail" type. This mode of co-operation enables the insert (3) to slide longitudinally inside the insertion canal formed when the two branches (1, 2) are assembled together. This "dovetail" type coupling prevents the branches (1, 2) from coming apart and separating once the insert is engaged. Once the insert (3) is inserted between the two branches (1, 2), the resulting assembly forms a solid and uninterrupted tubular element (apart from the medullary canal for passing the screwdriver). Even when the elements are made of a plastic material, the assembly is strong enough to withstand the forces exerted by the surgeon during the adjustment of the positions of the interconnected vertebrae.

At its proximal end, the insert (3) has a cap-receiving zone (15) designed to receive a screw-on cap (36) suitable for being screwed onto the head of the screw (4), and to lock the intervertebral rod (35) once said rod has been put in place.

The screw (4), which is made of metal (e.g. of titanium) has a head (22) that, in the example described, forms a ball-type coupling for coupling the head to the threaded portion of the screw. Said head has longitudinal extensions (23, 24) that, in the non-limiting example described, are fork-shaped. The branches (1, 2) have spaces (25, 26) of shape complementary to the shape of said extensions (23, 24).

When the extensions (23, 24) are received in the complementary cavities, they contribute to the strength of the proximal end, and they avoid the risks of the head of the screw becoming disengaged or of breaking that are observed in the prior art solutions during manipulation by the surgeon using the branches as correction levers. The extensions (23, 24), which are generally made of metal, are embedded in the material of which the branches and the insert are made so as to from a reinforced assembly that is solid (apart from the medullary canal).

In the example described, the head of the screw also has two radial grooves (27, 28) parallel to a diametrical axis passing through the axis of the intervertebral rod (35). These recesses (27, 28) are suitable for co-operating with lips (29, 30) formed on the inside surfaces of the proximal ends of the branches (1, 2). This mode of coupling makes it possible: a) to hold the screw (4) while it is being inserted into the vertebra; and b) to release the head of the screw, after the operation, by tilting the two branches after the ring and the insert have been removed.

In addition, the head of the screw (4) has two break zones (31, 32) below (on the proximal side of) said extensions (23, 24). These break zones are designed to separate the extensions from the screw, once the operation is finished, and to avoid leaving unnecessary metal parts in the body. These break zones (31, 32) are constituted by notches of depth and geometrical shape that are determined to enable a clean break to be obtained when a lateral force exceeding a threshold value is exerted on one of the extensions using a specific instrument.

Figure 2:
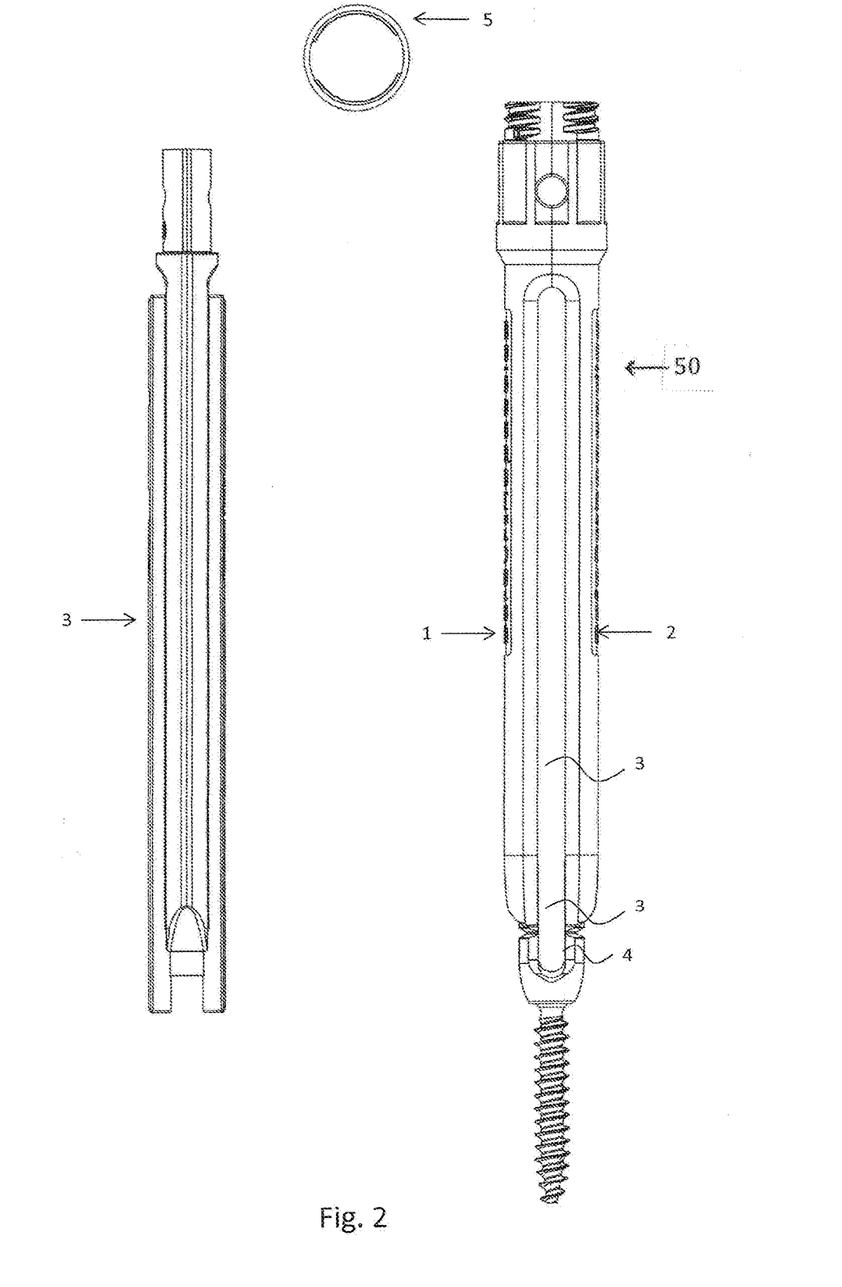
FIG. 2 is a view of the fitting tube carrying the screw; the ring and the insert being shown as not fitted to the fitting tube.

FIG. 2 shows the two branches (1, 2) assembled together to form a tubular element inside which the insert (3) can be slid. When the two branches (1, 2) are assembled together, they allow a guide slot (33) to remain for guiding an intervertebral rod, this slot (33) opening out into the canal (34) of the screw (4).

Figure 3:
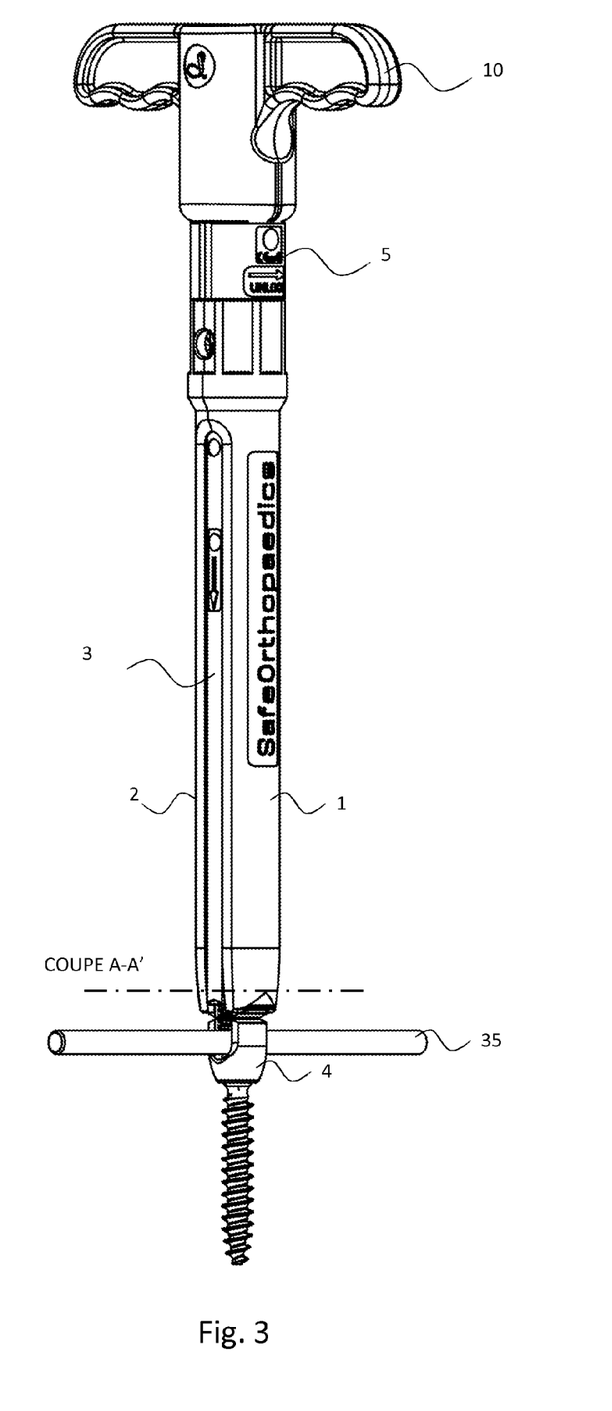
FIG. 3 is a view of the fitting tube carrying the screw, the ring, the insert and the handle.

FIG. 3 is a view showing the two branches (1, 2) assembled together and secured together firstly by the insert (3) and secondly by the ring (5). The handle (100) is screwed onto the distal ends of the two branches to make it possible to exert a longitudinal force on the intervertebral rod (35), via the insert (3).

Figure 4:
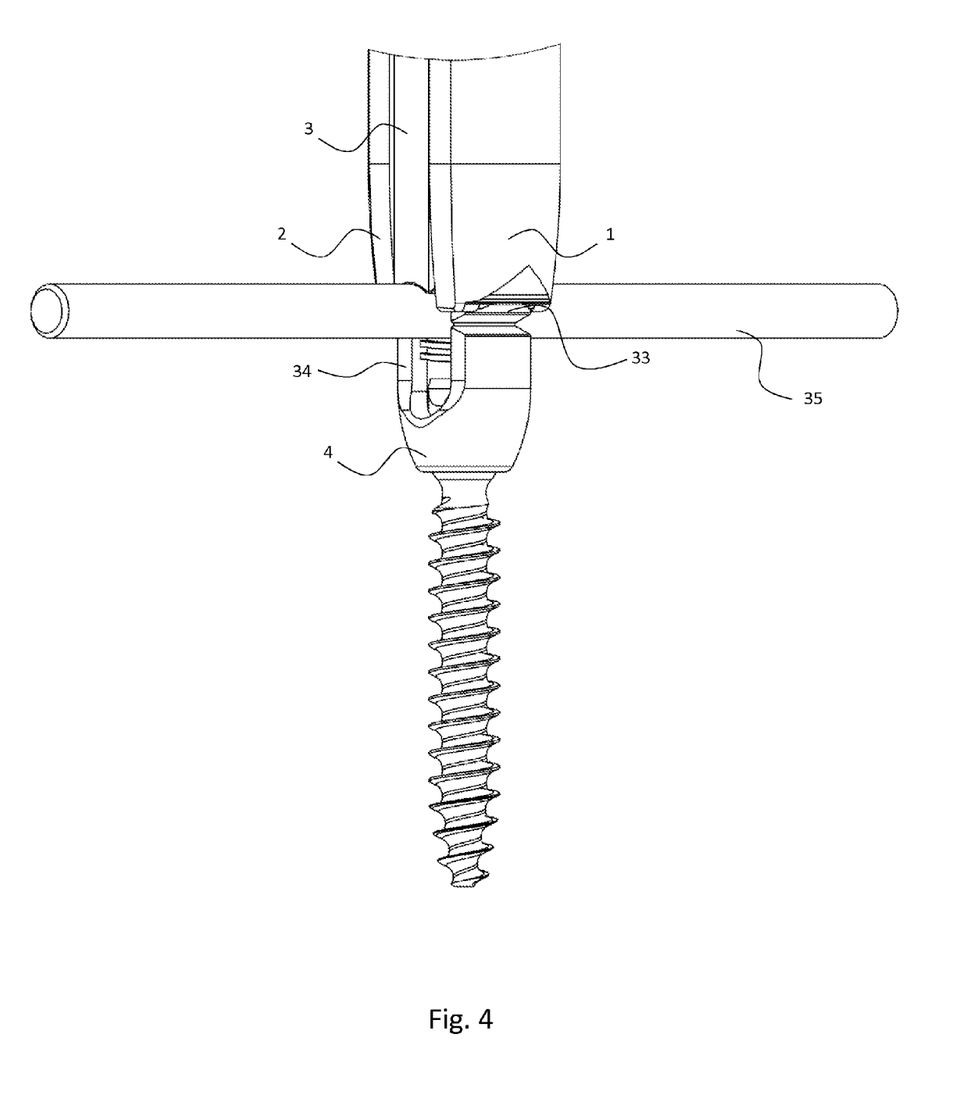
FIG. 4 is an enlarged view of the fitting tube carrying the screw, the ring, the insert and an intervertebral rod.

As shown in FIG. 4, the insert (3) makes it possible to exert thrust on the intervertebral rod (35), as engaged in said slot (33), which guides it into its final position in the canal (34). Once in place, a screw-on cap (36) is placed on the screw by means of the insert (3), and is then tightened by a screwdriver shank passing through the medullary canal of the insert (3).

Figure 5:
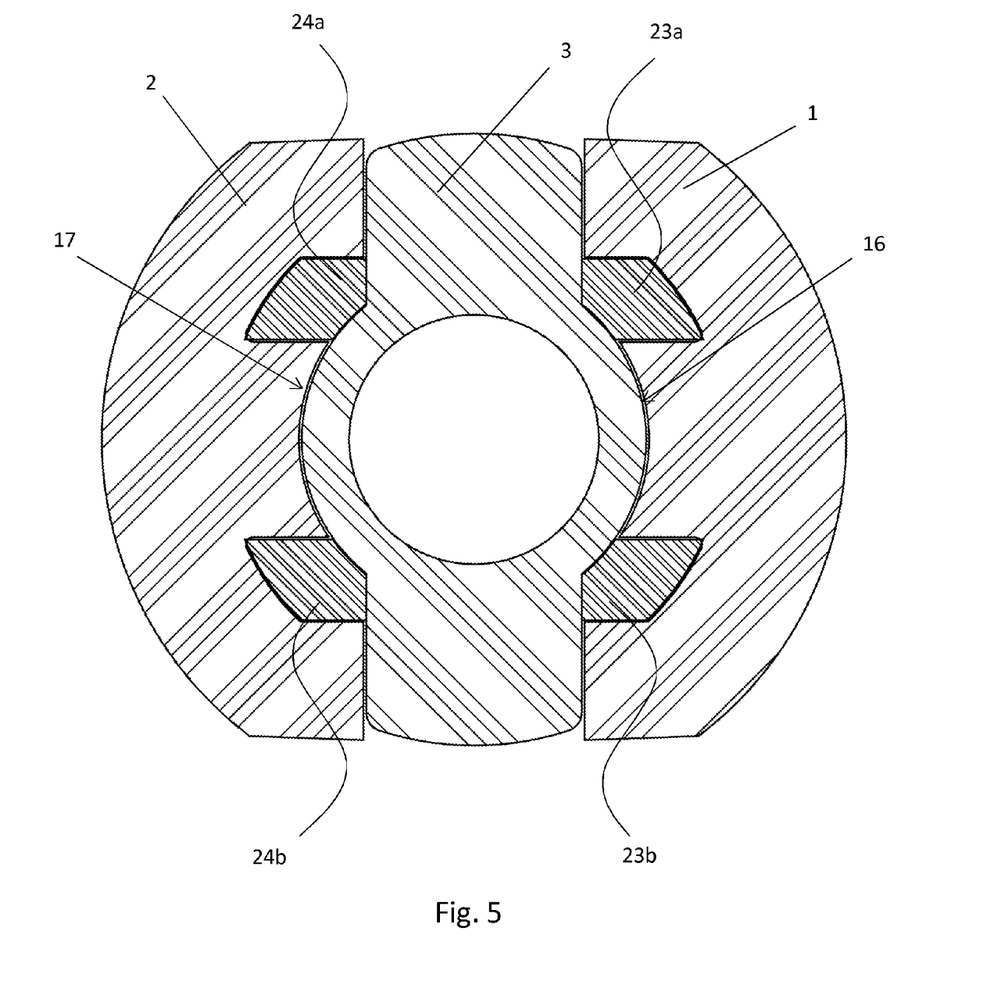
FIG. 5 is a cross-sectional view of the kit at the extensions of the head of the screw, on a section plane AA'.

FIG. 5 is a cross-section view of the kit at the extensions of the head of the screw. Each of the metal extensions (23, 24) of the head of the screw forms two prongs (23a & 23b, and 24a & 24b) coming to engage in cavities defined firstly by the branches (1, 2) and secondly by the insert (3).

Figure 6:
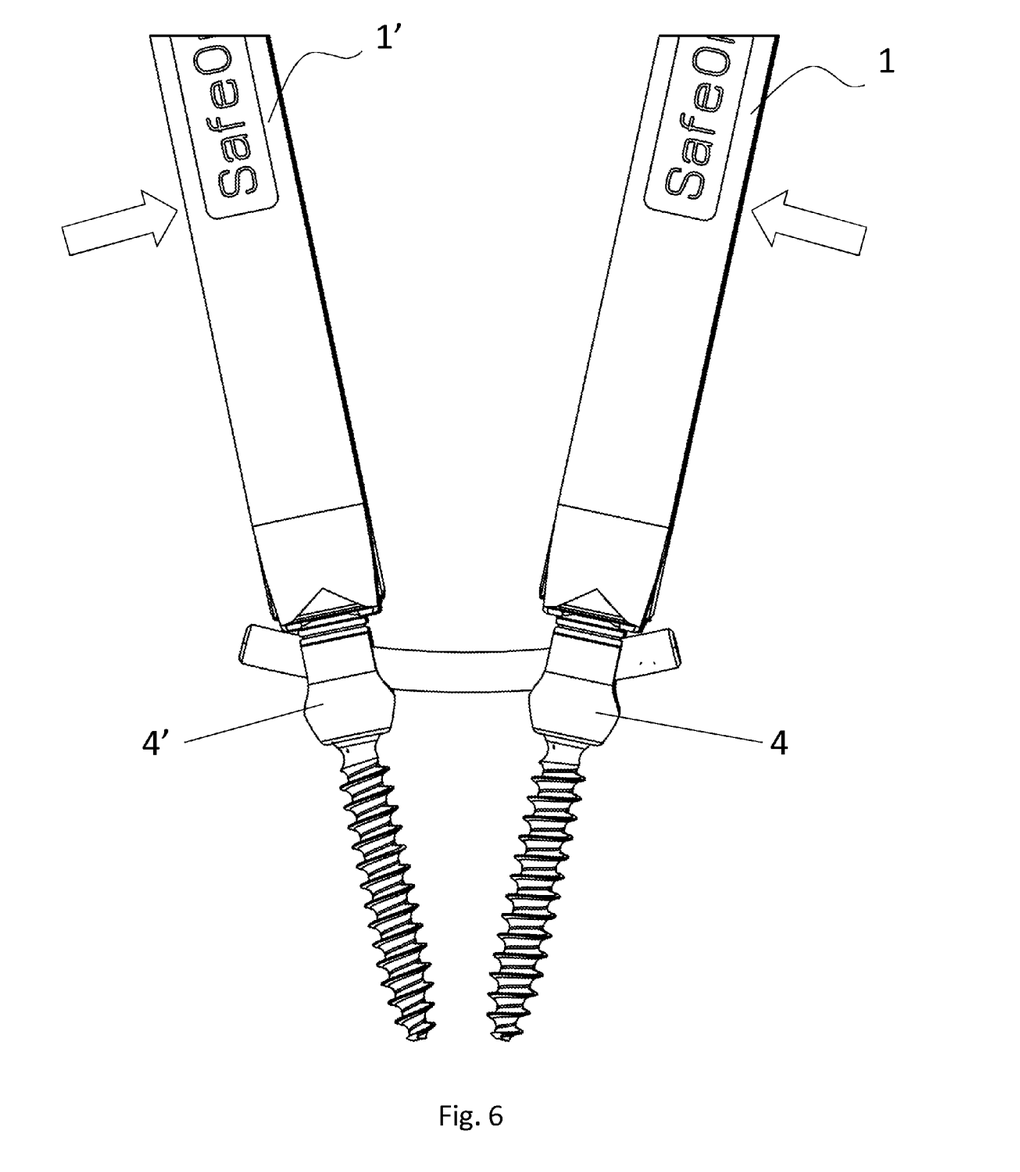
FIG. 6 is a diagrammatic view of two kits during the stage for positioning two vertebrae relative to each other.

These metal extensions (23, 24) thus come to reinforce this fragile zone where high mechanical stresses are exerted when the surgeon uses the branches (1, 2) as levers for shifting the vertebrae (see FIG. 6).

Figure 7:
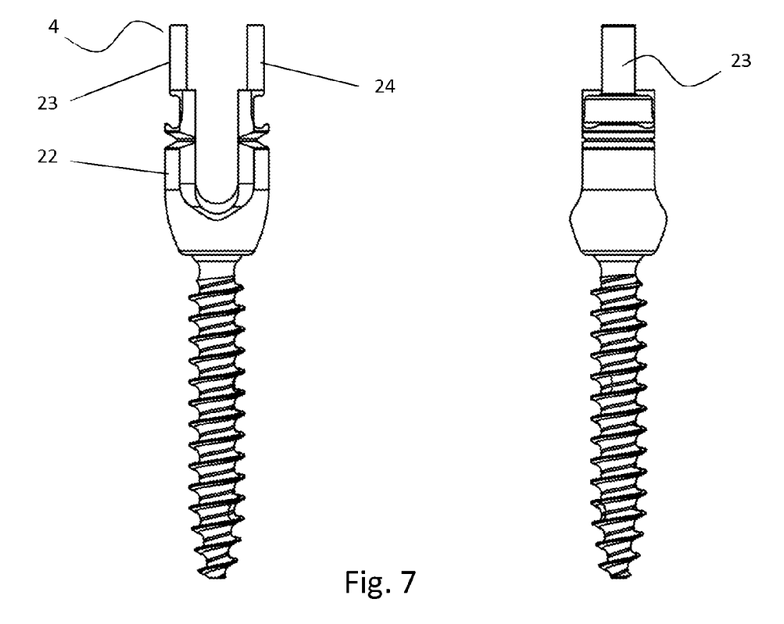
FIGS. 7 to 9 show variant embodiments of the extension of the head of the screw.
Figure 8:
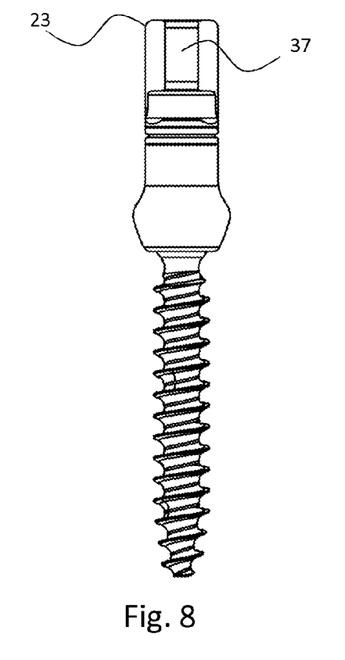
Figure 9:
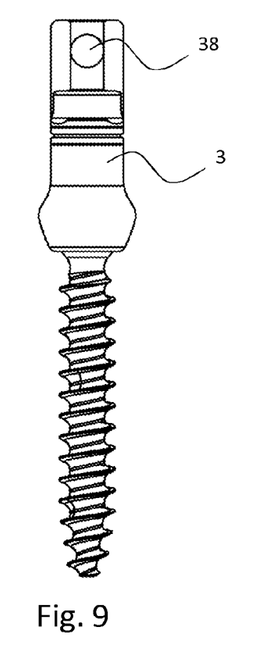

FIGS. 7 to 9 show variant embodiments of the head of the screw.

FIG. 7 shows a first variant in which the extensions (23, 24) are constituted by a single tab on either side of the insertion canal into which the intervertebral rod is inserted. It is recalled that, in the example shown in the preceding figures, each of the extensions (23, 24) is constituted by a pair of tabs forming a fork, the pairs being disposed on either side of the insertion canal into which the intervertebral rod is inserted.

FIGS. 8 and 9 show two variants in which the extensions (23, 24) are constituted by a single semi-tubular portion on either side of the insertion canal into which the intervertebral rod is inserted. These semi-tubular portions have rectangular (37) or circular (38) orifices for fastening to a protuberant zone provided on the inside surface of the proximal end of each of the branches (1, 2). These protuberant zones have complementary shapes and make it possible to connect to branches (1, 2) on the extensions (23, 24) of the head of the screw (4). In particular, they may replace the lips (29, 30) and the groove (27, 28) of the screw. These protuberances hold the head of the screw (4) when the two branches (1, 2) come to "clamp" the head of the screw, while also facilitating releasing the branches once the operation is finished.

The invention claimed is:

1. A surgical kit for fastening vertebrae via the posterior approach or via the posterolateral approach, the kit comprising:
at least one vertebral or pedicle screw, and a fitting tube co-operating with said screw, wherein said screw comprises a screw head having two lateral arms;
said fitting tube having two rigid branches, each of said two branches having, on the inside face of a proximal end, at least one shoulder of shape complementary to the shape of an indentation provided on either side of a screw head, for allowing said screw to be taken hold of, or to be released by moving the ends of said rigid branches apart;
the kit further comprising a retractable securing insert for securing together said branches;
wherein the lateral arms of said screw head have at least two longitudinal extensions extending in the distal direction beyond the indentation of the respective arm;
wherein each of said two branches has a cavity configured to receive one of said extensions, said cavity being situated above the shoulder and opened to the inner face of the respective branch, said cavity having a complementary shape to an outer surface of the respective extension,
wherein each of said extensions being configured to enable their insertion into the respective cavity delimited by an outside surface of the proximal end of said retractable securing insert, when said retractable securing insert is fully engaged in said fitting tube.

2. A surgical kit according to claim 1, wherein the head of the screw is provided with two break zones below said extensions.

3. A surgical kit according to claim 1, wherein the retractable securing insert has longitudinal fastening means arranged to be dovetail shaped so as to come into engagement with complementary slideways provided in said rigid branches.

4. A surgical kit according to claim 1, wherein each of the distal ends of the branches is also provided with a tenon coming to be received in a complementary cavity provided in the other branch.

5. A surgical kit according to claim 1, wherein said screw head is provided with fork-shaped longitudinal extensions, and in that the branches are provided with spaces of shape complementary to the shape of said extensions.

6. A surgical kit according to claim 1, wherein each of the at least two longitudinal extensions comprise metal, said at least two longitudinal extensions forma two prongs configured to engage in cavities defined by respective ones of the branches, and by the insert.

7. A surgical kit according to claim 1, wherein the head of the screw is further provided with a radial groove suitable for co-operating with lips formed on the inside surfaces of the proximal ends of the branches.

8. A surgical kit according to claim 1, wherein said branches and said insert are made of a molded plastics material and are for single use.

* * * * *